US005516940A

United States Patent [19]
Katti et al.

[11] Patent Number: 5,516,940
[45] Date of Patent: May 14, 1996

[54] MULTIFUNCTIONAL LIGAND FOR USE AS A DIAGNOSTIC OR THERAPEUTIC PHARMACEUTICAL

[75] Inventors: Kattesh V. Katti; Wynn A. Volkert; Alan R. Ketring; Prahlad R. Singh, all of Columbia, Mo.

[73] Assignee: Curators of the University of Missouri, Columbia, Mo.

[21] Appl. No.: 235,355

[22] Filed: Apr. 29, 1994

Related U.S. Application Data

[63] Continuation-in-part of Ser. No. 50,253, Aug. 26, 1993, abandoned, which is a continuation-in-part of Ser. No. 694,142, May 1, 1991, abandoned.

[51] Int. Cl.$^6$ .................. C07F 9/50; C07F 9/53; C07D 241/04
[52] U.S. Cl. .................. 564/14; 252/625; 544/225; 544/229; 544/337; 556/13; 556/14; 556/45; 556/81; 564/12; 564/251; 564/310; 564/464
[58] Field of Search .................. 564/12, 14, 251, 564/310, 464; 252/625; 424/1.11, 1.49, 1.77; 514/63, 118, 639, 649, 664, 85, 492, 502; 544/225, 229, 337; 556/13, 14, 45, 81

[56] References Cited

PUBLICATIONS

Majoral III et al. "Heterocycles containing phosphorus XXXII", etc. abst in chem abst. 88(7) 50967h.
Spencer et al. *Radionuclides in therapy*, Boca Raton, FL: CRC Press, 1987.
Schlom "Basic principles and applications of monoclonal antibodies in the management of carcinomas" *Canc. Res.* 46:3225–3238, 1986.
Saenger et al. "Radiotherapeutic agents: properties, dosimetry and radiobiologic considerations" *Semin. Nucl. Med.* 9:72–84, 1979.
Volkert et al. "Therapeutic Radionuclides: Production and decay property considerations" *J. Nucl. Med.* 32:1991.
Schubiger and Hasler, *Radionuclides for therapy*, Basel, Switzerland: Hoffman–LaRoche & Co., Ltd. 1986.
Mausner et al., "Production and use of prospective radionuclides . . ." in *Radiolabeled monoclonal antibodies for imaging and therapy*, edited by Srivastava, S. C. NY: Plenum Publishing Corp. 1988, pp. 149–163.
Andres et al. "Radionuclides for therapy: a review" In: *Radionuclides for Therapy*, edited by Schubiger et al. Switzerland: Editones–Roche, 1986. pp. 9–20.
Kozak et al., "Nature of bifunctional chelating agent used for radioimmunotherapy. . ." *Cancer Res.* 39:2639–2644, 1989.
Hnatowich, "Antibody radiolabeling, problems and promises" *Nucl Med Bio Int J Radiat Appl Inst* [B] 17:49–55, 1990.
Rao et al., "Dependence of immunoreactivity and tumor uptake . . ." *J Nucl Med* 29:815, 1988.

Deshpande et al. "Yttrium–90–labeled monoclonal antibody for therapy: labeling by a new macrocyclic bifunctional chelating agent" *J Nucl Med* 31:473–479, 1990.
Washburn et al. "A new bifunctional chelate reagent for labeling monoclonal antibodies with Y." *J Nucl Med.* 31:824, 1990.
Meares et al. "Chelate radiochemistry: Cleavable linkers lead to altered levels of radioactivity in the liver" *Int J Cancer* 2:99–102, 1988.
Naruki et al. "Differential cellular catabolism of . . ." *Nucl. Med. Bio; Int J Radiat Appl Inst* [B] 17:201–207, 1990.
Parker "Tumour targeting with radiolabelled macrocycle—antibody conjugates" *Chem Soc Rev* 19:271,291, 1990.
Abrams et al. "Synthesis and crystal and molecular structure of a Technetium–Hydralazino complex . . ." *Inorg Chim Acta* 173:133–135, 1990.
Abrams et al. "Technetium–99m–human polyclonal IgG radiolabeled via the Hydrazino Nictinamide derivative for imaging focal sites . . ." *J Nucl Med* 31:2022–2028, 1990.
Kung et al. "Current and future radiopharmaceuticals for brain imaging with single photon emission computed tomography" *Sem Nucl Med* 20:290–302, 1990.
Dewanjee, "The chemistry of Tc–labeled radiopharmaceuticals" *Sem Nucl Med* 20:5–27, 1990.
Nishida et al. "ESR Spectra of Seven–coordinated Pentagonal Bipyramidal Copper (II) Complexes" *Inorganica Chimica Acta* 45:L113–L114 (1980).
Noth and Thorn, "The Stabilization of Tris (hydrazino) phosphane by Complex Formation" (not translated) *B: Anorg. Chem., Org. Chem.* vol. 34B, No. 6, pp. 659–661 (1981).
Maisch, "The Stabilization of Phosphanes . . ." (not translated) *B: Anorg. Chem., Org. Chem.,* vol. 34B, No. 6, pp. 784–789 (1979).
Scola et al., "N,N–Disubstituted P–phenylphosphothioic diamides." Abst. in Chem. Abst. CA 69(25): 106808.
Horn et al. "Darstellung von thiophosphoryltrihydrazide, etc." Chemische Berichte 100(7) (1967) pp. 2258–2260.
Majoral I "Heterocycles Contenant, Du Phosphore—XXIX" *Tetrahedron* vol. 32 pp. 2633–2644 (1976).
Majoral II "Heterocycles Containing Phosphorus, Part 30." *J. Chem. Soc.* Perkins Trans. I, Part II (1976) pp. 1993–2596.
Bakhtyarova et al. "Reaction of Monochloroacetic acid with diamides, etc." Abst. in *Chem Abst* 99(25) 212591n.
Al–Rawi et al., "Carbon 13 chemical shift, etc." Abst. in *Chem Abst.* 105(5): 42955g.
Grapov et al. "Some reactions of phosphorus thio acid dihydrazides, etc." Abst. in *Chem. Abst.* 87(19): 152323s.
Huang et al., "Polymers containing Phosphorus, etc." abst. in Chem. Abst. 76(20): 113579h.

*Primary Examiner*—Peter O'Sullivan
*Attorney, Agent, or Firm*—Kohn & Associates

[57] ABSTRACT

A compound and method of making a compound for use as a diagnostic or therapeutic pharmaceutical comprises either a phosphorous or germanium core and at least two hydrazine groups forming a ligand for bonding to a metal extending from the phosphorous or germanium core.

13 Claims, No Drawings

MULTIFUNCTIONAL LIGAND FOR USE AS A DIAGNOSTIC OR THERAPEUTIC PHARMACEUTICAL

GRANT REFERENCE

Research in this application was supported in part by a grant from the Department of Energy (DE-FG02-89ER60875) to one of the inventors (Wynn A. Volkert). The Government has certain rights in the invention.

This application is a continuation-in-part of application Ser. No. 050,253, filed Aug. 26, 1993, now abandoned, which is a continuation-in-part of application Ser. No. 07/694,142, filed on May 1, 1991, now abandoned.

TECHNICAL FIELD

The present invention relates to pharmaceuticals, especially radiopharmaceuticals, for use as diagnostic and therapeutic agents. More specifically, the present invention relates to a compound and method of synthesizing a compound which is a multidentate ligand that complexes with transition metal radionuclides for use as diagnostic or therapeutic radiopharmaceuticals.

BACKGROUND OF THE INVENTION

Radiotherapy using "non-sealed sources" by way of radiolabeled pharmaceuticals has been employed for several decades. Spencer et al., 1987; Schlom, 1986; Saenger, 1979. Unfortunately, less than a handful of therapeutic radiopharmaceuticals are currently in routine use, as being approved by the FDA. There has been renewed interest in developing new agents due to the emergence of more sophisticated molecular carriers, such as monoclonal antibodies that are capable of selectively targeting cancerous lesions. In addition, the identification of several different radionuclides Volkert et al., 1991; Schubiger and Hasler, 1986; Mausner et al., 1988; Andres et al., 1986 with different chemical properties that have physical decay properties that are desirable for therapeutic application have further spurred development of new agents.

Despite some successes in treatment of specific malignant diseases and increased research and development activities in this area, many problems remain with the use of such treatments. For example, it has been difficult in most cancers to provide acceptable selectivity in radiation doses delivered to target tissues relative to normal tissues. Successful development of new therapeutic radiopharmaceuticals requires improved localization of these agents in target tissues and/or increasing rates of clearance from non-target tissues. In both of these cases, it is imperative that the therapeutic radionuclide remain firmly associated with the radioactive drug in vivo for extended periods of time. These periods of time can extend from a few hours up to several days, depending on the pharmacokinetics and physical half-life of the radionuclide. No single radionuclide can be appropriate in formulating therapeutic agents since different half-lives and the energy of emitted particles is required for different applications [Volkert et al., 1991; Schubinger and Hasler, 1986; Mausner et al., 1988; Andres et al., 1986] thereby making it essential that radiopharmaceuticals with different radionuclides be available.

Therapeutic agents have been primarily labeled with beta-particle emitting radionuclides. Most of the promising radionuclides are produced in nuclear reactors, however, some are accelerator produced. [Volkert et al., 1991; Schubiger and Hasler, 1986; Mausner et al., 1988; Andres et al., 1986]. Several different chelating structures have been employed to maintain the association of these beta emitters with the drug. [Kozak et al., 1989; Hnatowich, 1990; Rao et al., 1988; Deshpande et al., 1990; Washburn et al., 1990]. Many of these structures are not sufficiently stable and most, if not all, do not provide appropriate routes or rates of clearance of radioactivity from non-target tissues. [Meares et al., 1988; Naruki et al., 1990]. Accordingly, there is a delivery of high radiation doses to normal tissues and a reduction of the therapeutic ratio. This lowers the amount of radiation dose that can be safely delivered to a target tissue. Development of new radionuclide that link the radioactive metal to the radiopharmaceutical is necessary. Further, new approaches must be taken in order to identify radio-labeling techniques that produce chelates that are highly stable in vivo but have improved clearance characteristics from normal tissues.

Bi-functional chelating agents have been used to form stable metal complexes that were designed to minimize in vivo release of the metallic radionuclide from the radiopharmaceutical. For example, diethyltriaminepentaacetic acid (DTPA) forms rather stable chelates with a variety of metals. However, coupling of this ligand to monoclonal antibodies by one of its five carboxyl groups resulted in unacceptable in vivo stability with a variety of radionuclides [Parker, 1990]. Linking of this compound by a side group attached to one of the carbon atoms on an ethylene bridging group provides improved stability in vitro and in vivo. The stability characteristics of these compounds are not ideal resulting in poor clearance of activity from certain non-target organs are poor.

Chelating agents based on diamidodithiol and triamidomonothiol backbones are used for forming small and stable hydrophilic complexes with several beta-emitting transition metals. These were developed by Fritzberg and colleagues [1988] for labeled monoclonal antibody products for diagnostic and therapeutic applications. These chelates provide improved clearance characteristics from the liver; however, kidney retention of activity when using Fab or (Fab)$_2$ fragments of monoclonal antibodies labeled with these radionuclide chelates is higher than desirable.

A macrocyclic tetramine-based chelating agent that also has four methylene carboxylate side atoms has been used to form a copper complex that has a high in vitro and in vivo stability when linked to monoclonal antibodies. This chelate was first described for monoclonal antibody bioconjugation by Meares and coworkers. [Deshpande et al., 1990; Washburn et al., 1990] The chelate is rather large. Clearance of activity from non-target organs has not been shown to be more efficient than the chelates mentioned above.

Recently, a mono-hydrazide bifunctional chelating agent has been described that forms somewhat stable $^{99m}$Tc complexes. [Abrams et al., 1990a: Abrams et al., 1990b] This particular ligand can be first attached to a protein and then binds to $^{99m}$Tc as it is chelated with glucoheptonate in aqueous solutions at or near neutral pH. [Abrams et al., 1990b] Other work with mono-hydrazide ligands with other Tc$^V$ complexes demonstrates the reaction of the monohydrazides at the axial position with Tc$^V$=O to form similar mondentate linkages. [Abrams et al., 1990a] The in vitro and in vivo stability of these types of chelates has not been adequately described in the literature.

Applicant has synthesized a series of multi-dentate ligands derived from a phosphorous or germanium core utilizing hydrazine groups as arms of these ligands to form small but stable and well defined complexes with transition metal radionuclides. Unlike prior art chelates, these chelates show good stability in both aqueous solutions, serum, and other body fluids.

SUMMARY OF THE INVENTION

In accordance with the present invention, there is provided a compound for use as a diagnostic or therapeutic pharmaceutical, the compound comprising a phosphorous or germanium core and at least two hydrazine groups forming a ligand for bonding to a metal extending from the phosphorous or germanium core.

The present invention further provides a method of making the compound for use as a diagnostic therapeutic pharmaceutical, the method including the following reaction

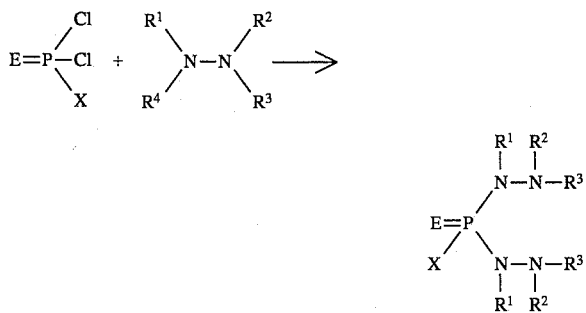

Wherein
$R^1$ is H and
X is

or
alkyl (Me, Et, n- or i- propyl, n-, i- or t-butyl, n- or cyclohexyl),
alkyl amine [primary and secondary, —NMe$_2$, MHMe, —(CH$_2$)$_n$NMe$_2$, —(CH$_2$)$_n$NHMe, —(CH$_2$)$_n$NH$_2$],
alkoxy [O(CH$_2$)$_{2n}$CH$_3$)$_n$],
aromatics (—C$_6$H$_4$R$^7$ wherein $R^7$ is H, NH$_2$ COOH, NCS, CHO, activated esters, acid anhydrides, N-hydroxy succinimide, and SiMe$_3$).
$R^2$, $R^3$, $R^4$, $R^6$ are all the same or different being H,
alkyl (Me, Et, n- or i-propyl, n-, i- or t-butyl, n- or cyclohexyl),
alkyl amine [primary and secondary, —NMe$_2$, NHMe, —(CH$_2$)$_n$NMe$_2$, —(CH$_2$)$_n$NHMe, —(CH$_2$)$_n$NH$_2$],
alkyoxy [O(CH$_2$)$_n$CH$_3$ or —(CH$_2$)$_n$OCH$_3$]. $R^5$ is the same or different than $R^2$, $R^3$, $R^4$, $R^6$ and is all the substitutes defined for X except for the hydrazine group. E is O, S, NSiME$_3$, a lone pair of electrons, or NC$_6$H$_4$R$^8$ wherein $R^8$=H, NH$_2$, COOH, NCS, CHO, N-hydroxysuccinimide, activated esters or acid anhydrides.

Similar reactions of germanium halides (eg., GeCl$_4$, RGeCl$_3$) with hydrazine reactants as defined above for the phosphorous core produced germanium hydrazides containing up to four hydrazine units.

DETAILED DESCRIPTION OF THE INVENTION

Generally, the present invention provides a compound for use as a diagnostic or therapeutic pharmaceutical; however, they may also be used for other pharmaceutical applications, including MRI contrast agents. The compound includes a phosphine core and at least two hydrazine groups forming a ligand for bonding to a metal extending from the phosphorous or germanium core. That is, the invention provides phosphorous and germanium hydrazide ligand systems containing between 2 and 4 hydrazine units for use in forming complexes with a variety of transition metals that have high in vitro and/or in vivo stability.

The phosphorous and germanium ligands were chosen since the hydrazine arms linked directly to phosphorous atom provides a plethora of electron density on the terminal hydrazine-N-atoms that promote formation of highly stable nitrogen-metal bonds. This occurs even with the transition metals in their higher oxidation states, such as Re$^v$. The utilization of at least two hydrazine groups for metal bonding produces complexes that are more stable than the metal complexes with only one hydrazine arm.

The ligand is complexed with the transition metal, generally from the group including Fe, Mn, Re, Re, Pd, Rh, and $^{99m}$Tc. These complexes contain a 1:1 metal to ligand ratio which is formed making the resulting chelates small and well-defined. These specific combinations permit the formation of the complexes in a one step, high yield reaction as described below, especially for use with readily available chemical forms of the radionuclides. Other metals suitable for chelating are copper and cobalt.

For example, $^{99m}$TcO$_4^-$, ReO$_4^-$ chelates or PdCl$_2$ can be used. It has been determined that these types of ligands form highly stable chelates with a variety of transition metals that have radioactive isotopes that have potential for formulation of new therapeutic uses, such as $^{186}$Re, $^{188}$Re, $^{109}$Pd, $^{105}$Rh, etc., or for diagnostic use such as with $^{99m}$Tc radiopharmaceuticals.

For example, Fe and Mn are paramagnetic elements and have potential application in chelate form as MRI contrast imaging agents. Stable Mn and Fe chelates with the P and Ge hydrazine ligands with appropriate substituents can be formulated.

The chelates made in accordance with the present invention have been found to be stable in aqueous solutions, serum and other body fluids. This is critical to solve the problems of prior art agents which did not form stable chelates thereby having an inherent loss of control of localization of the radionuclide paramagnetic metal. Further, compounds made in accordance with the present invention can be chemically modified, as discussed below, to provide for specificity of localization, increased physical half-life of the radionuclide, improved pharmacokinetics, and increased selectivity of target tissues, such as tumors, over normal tissue, such as bone marrow, kidney, GI tract, liver etc.

The compounds made in accordance with the present invention are not only stable in neutral aqueous solutions, but have also been found to be stable in acidic and basic aqueous media. Again, this is critical with regard to localization of the compound in areas of the body having different pH's, as well as being stable through different administration routes, such as oral administration.

More specifically, the bis-hydrazine ligand made in accordance with the present invention can be characterized by the following formula:

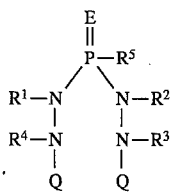

Formula I wherein $R^1$, $R^2$, $R^3$, $R^4$, are all the same or H, different and are alkyl (Me, Et, n- or i-propyl, n-, i- or t-butyl, n- or cyclohexyl, —$CH_2COOH$, —CH(OH) $CH_2OH$), alkylamine [primary and secondary, —$NMe_2$, NHMe, $(CH_2)_nNMe_2$, $(CH_2)_nNHMe$, —$(CH_2)_nNH_2$], alkoxy [—$O(CH_2)_nCH_3$ or $(CH_2)_nOCH_3$, —$(CH_2)_n$—COOH or —$(CH_2)_nSH$], aromatics (—$C_6H_4R$ wherein R=H, $NH_2$, COOH, OH, NCS, CHO, activated esters, acid anhydrides, N-hydroxy succinamide, and $SiMe_3$). $R^5$ is H, $OCH_3$—CH(OH)—$CH_2OH$, Me or Ph. E is O, S, —$NSiMe_3$, a lone pair of electrons or $NC_6H_4R$ wherein R=H, OH, $NH_2$, COOH, NCS, CHO, N-hydroxy succinamide, activated esters or acid anhydrides.

As used herein, $n$ is the number 1 to 6; and Q is H, —$CH_2Ph$ or =CHPh wherein in each instance Ph is unsubstituted or substituted with OH, COOH, alkyl wherein alkyl are from 1 to 4 carbon atoms, $NH_2$, NH (alkyl $C_{1-4}$) or NH(Alkyl $C_{1-4})_2$, or halogen such as chlorine, fluorine, bromine and iodine or Q can be —$CH_2$piperazino or CH piperazino.

The tris-hydrazine ligand made in accordance with the present invention can be characterized by the following:

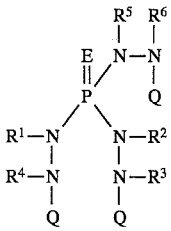

Formula II wherein $R^1$, $R^2$, $R^3$, $R^4$, are all the same or different and are

H, alkyl (Me, Et, n- or i-propyl, n-, i- or t-butyl, n- or cyclohexyl), alkylamine [primary and secondary, —$NMe_2$, NHMe, $(CH_2)_nNMe_2$, $(CH_2)_nNHMe$, —$(CH_2)_nNH_2$], alkoxy [—$O(CH_2)_nCH_3$ or $(CH_2)_nOCH_3$], aromatics (—$C_6H_4R$ wherein R=H, $NH_2$, COOH, NCS, CHO, activated esters, acid anhydrides, N-hydroxy succinamide, and $SiMe_3$). $R^5R^6$ is H, Me or Ph. E is O, S, —$NSiMe_3$, a lone pair of electrons or $NC_6H_4R$ wherein R=H, $NH_2$, COOH, NCS, CHO, N-hydroxy succinamide, activated esters or acid anhydrides. Q and $n$ are as defined in Formula I and further each of $R^1$ to $R^5$ can be defined as in Formula I and $R^6$ can be the same as $R^1$ to $R^5$ as defined in Formula I.

The germanium hydrazide ligands made in accordance with the present invention can be characterized by the following:

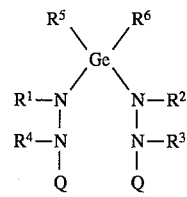

wherein $R^1$, $R^2$, $R^3$, $R^4$, are all the same or different and are

H, alkyl (Me, Et, n- or i-propyl, n-, i- or t-butyl, n- or cyclohexyl), alkylamine [primary and secondary, —$NMe_2$, NHMe, $(CH_2)_nNMe_2$, $(CH_2)_nNHMe$, —$(CH_2)_nNH_2$], alkoxy [—$O(CH_2)_nCH_3$ or $(CH_2)_nOCH_3$], aromatics (—$C_6H_4R$ wherein R=H, $NH_2$, COOH, NCS, CHO, activated esters, acid anhydrides, N-hydroxy succinamide, and $SiMe_3$). $R^5$, $R^6$ are Cl, Me, Ph, $R_1N$—$NH_2$ or $NC_6H_4R$ wherein R,$R_1$=H, $NH_2$, COOH, NCS, CHO, N-hydroxy succinamide, activated esters or acid anhydrides and are all the same or different. Q and $n$ are as defined as in Formula I and further $R^1$ to $R^6$ can be defined as in Formula II.

The above formulas characterize the present invention as being very modifiable in order to specifically tailor the ligand for chelation with a specific radionuclide and localization at a specific target organ.

For example, the ligand can be conjugated to protein or antibodies and can use side chains previously used for linking monoclonal antibodies. [Parker, 1990] For example, conjugation reactions can involve reactive groups such as benzyl isothiocyanate, bromoacetamide, activated esters, N-hydroxysuccinimides, cleavable ester linkages, and aldehydes. [Parker, 1990] In the case where E is a lone pair of electrons on the phosphorous atom, attachment of the chelate or the hydrazide ligand to proteins or other molecules already containing an azido group can be brought about by the Standinger reaction. The conjugation reaction can occur using any of the R groups attached to the nitrogens on one of the hydrazine side arms or attached directly to the phosphorous or germanium atom. Accordingly, a single monoclonal antibody or several monoclonal antibodies can be added to the phosphorous or germanium hydrazine core to provide specificity of the binding of the ligand metal complex to specific surface antigen of target tissue.

As discussed above, other side chain modifications can be accomplished to make the chelate more polar and hydrophilic. For example, charged groups such as carboxyl or hydroxyl groups can be added at the various R groups appended to the hydrazine nitrogens. This additional small change in the compounds providing charged/polar groups increases the hydrophilic character of the resulting chelate. This will produce more rapid and selective clearance from the blood and nontarget tissue. This modification is highly desirable for the promotion of efficient clearance of radioactivity from nontarget tissues, such as blood, liver, kidney, and spleen following catabolism of conjugated radiolabeled monoclonal antibodies that are presently used for therapy.

Alternatively, the hydrophobicity of the chelate can be varied incrementally by varying the alkyl chain length of the side chains appended to the hydrazine nitrogens. For example, the R groups or the hydrazine side arms can be derivatized with hydrogen, methyl, ethyl, n- or i-propyl and n-, i-, or t-butyl. This is desirable because with some chelates, particularly those labeled with $^{99m}Tc$, an increase in the hydrophobicity of the chelate plays a major role in targeting uptake in selective tissues, such as in brain, heart and lung. Addition of alkyl groups to the chelating backbone increases the lipid solubility of the chelate. If the resulting chelate is neutral, either brain, heart, or lung imaging agents can be developed. [Kung et al., 1990] Similarly, if the overall chelate charge is +1 myocardial imaging agents can be developed. [Dewanjee, 1990] Modifying the hydrophobicity of chelates with beta-emitting radionuclides for therapy will also change the clearance and uptake properties in target and nontarget tissues.

An alternative to varying the alkyl chain length of the R groups appended to the nitrogens of the hydrazines is to add other hydrophobic functional groups, such as alkyl methoxy and alkyl methoxys to the R groups. The use of ether side chains instead of the alkyl side chains will increase lipophilicity but also improves the rate of clearance of the chelate from the blood and other non-target tissues. Other side chain modifications to increase hydrophilicity such as the addition ester groups or amide groups, can also be accomplished.

Another alternative modification of the chelate is to modify the charge or basic metal chelate core. It is possible to make the chelate with zero charge to produce a neutral hydrophilic chelate. For example, the bis-hydrazine ligand can be modified by the addition of a side chain other than hydrogen at the R groups attached to one of the hydrazine terminal nitrogens. Alternatively, negatively charged groups can be added, such as $(-CH_2)_n-SH$ or $(-CH_2)_n-COOH$.

All of the aforementioned modifications demonstrate the flexibility of compounds made in accordance with the present invention and further the ability to modify these compounds to alter the binding, elimination, and absorption of the compounds in order to tailor the compounds for specific organ targeting, dosing, and metabolism.

Compounds made in accordance with the present invention for use as diagnostic or therapeutic pharmaceuticals can be made by the following general reaction:

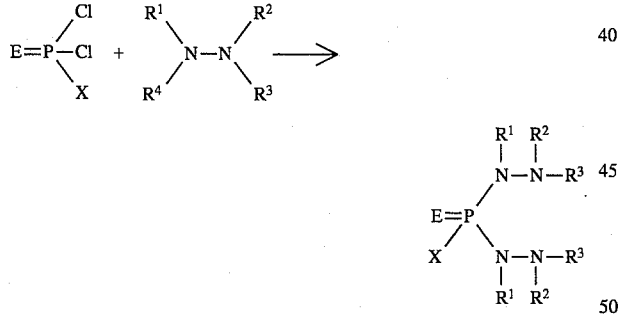

Wherein p1 $R^1$ is H and
X is

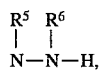

alkyl (Me, Et, n- or i- propyl, n-, i- or t-butyl, n- or cyclohexyl), alkyl amine [primary and secondary, $-NMe_2$, MHMe, $-(CH_2)_nNMe_2$, $-(CH_2)_nNHMe$, $-(CH_2)_nNH_2$], alkoxy $[O(CH_2)_{2n}CH_3)_n]$, aromatics ($-C_6H_4R^7$ wherein $R^7$ is H, $NH_2$ COOH, NCS, CHO, activated esters, acid anhydrides, N-hydroxy succinimide and $SiMe_3$). $R^2$, $R^3$, $R^4$, $R^6$ are all the same or different being H, alkyl (Me, Et, n- or i-propyl, n-, i- or t-butyl, n- or cyclohexyl), alkyl amine [primary and secondary, $-NMe_2$, NHMe, $-(CH_2)_nNMe_2$, $-(CH_2)_nNHMe$, $-(CH_2)_nNH_2$], alkyoxy $[O(CH_2)_nCH_3$ or $-(CH_2)_nOCH_3]$. $R^5$ is the same or different than $R^2$, $R^3$, $R^4$, $R^6$ and is all the substitutes defined for X except for the hydrazine group. E is O, S, $NSiMe_3$, a lone pair of electrons, or $NC_6H_4R^8$ wherein $R^8$=H, $NH_2$, COOH, NCS, CHO, N-hydroxysuccinimide, activated esters or acid anhydrides.

A solution of the appropriate phosphorous halide (e.g. $P(O)Cl_3$, $P(S)Cl_3$, $PCl_3$; $RPCl_2$ R=Ph,Me . . . ) in THF, toluene or chloroform was mixed with the solutions of lithiated or silyated hydrazines according to a set stoichiometry at 25° C. The reaction mixture was stirred at RT for 8–16 hours before the solvent was removed in the vacuum. The purifications of the phosphorous hydrazides were achieved either by recrystallization or through distillation under reduced pressure.

A solution of $GeCl_4$ or $RGeCl_3$ (R=Me,PH) in THF, toluene or $CHCl_3$ was mixed with the solutions of lithiated or silyated hydrazines according to a set stoichiometry at 25° C. The reaction mixtures were stirred at RT for 8–16 hour before the solvent was removed in vacuum. The germanium hydrazides were purified either by recrystallization or through distillations at reduced pressure.

The following are examples of ligands and chelates formed in accordance with the present invention.

EXAMPLE 1

LIGANDS SYNTHESIZED

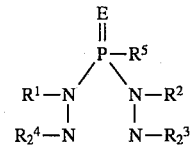

$R^5$ is

Ph, Me $R^1=R^2=R^3=R^4$=H; $R^1=R^4$=Me E=O, S, $NSiMe_3$ or electron pair

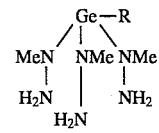

R=Cl; NMe—$NH_2$; Ph; Me

EXAMPLE II:

FORMATION OF COMPLEXES WITH RHENIUM

1. Re-BHP Complexes formed:

a. Complex I(Re)

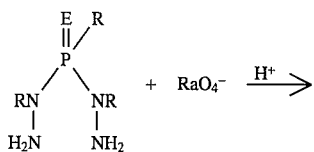
+ RaO₄⁻ $\xrightarrow{H^+}$

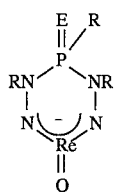

Characterized by ¹H and ³¹p NMR and C, H, N elemental analysis.

b. Complex II$_{(Re)}$

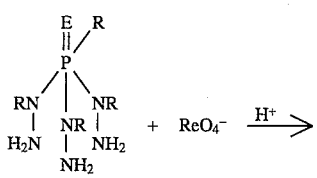
+ ReO₄⁻ $\xrightarrow{H^+}$

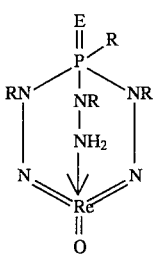

Characterized by ¹H and ³¹p NMR and C, H, N elemental analysis.

c. Complex III$_{(Re)}$
Formation of THP complexes with Re

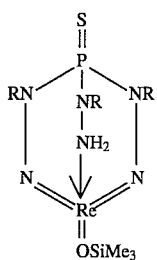

d. Complex IV$_{(Re)}$
Formation of BHP complexes with Re

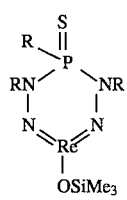

Characterized by ¹H and ³¹P NMR and C, H, N elemental analysis.

For the following examples unless otherwise stated, all reactions were carried out under anaerobic and anhydrous conditions using prepurified $N_2$ and conventional Schlenk techniques. Reagents such as $CO(ClO_4)_2 6H_2O$, $Cu(ClO_4)_2 6H_2O$, $P(S)PhCl_2$ and $PdCl_2$ were purchased from Aldrich Chemical Co., USA and were used without further purification. Phenylphosphodihydrazide 1 (Equation 1; Scheme 2; Scheme3) was prepared by the reaction of $PhP(S)Cl_2$ with methyl hydrazine. [Hnatowich, 1990; Rao et al., 1988]

Nuclear magnetic resonance spectra were recorded on a Bruker WH-500 Spectrometer. The ¹H NMR chemical shifts are reported in parts per million (ppm) downfield from external standard $SiMe_4$. The ³¹p NMR spectra were recorded with 85% $H_3PO_4$ as an external standard and positive shifts lie downfield of the standard. The structure of the compounds prepared are set forth in Equation 1 and Schemes 2 to 4 hereof.

Synthesis of Complex 2 (Scheme 2): To a solution of i (4.7 g; 20.25 mmol) in absolute ethanol (100 mL) was added dropwise with stirring at 0° C. a solution of $Co(ClO_4)_2 6H_2O$ (2.47 g; 6.74 mmol) also in absolute ethanol (50 mL). Upon completion of addition (30 minutes), a pink solid precipitated out. The mixture was stirred at 25° C. for 6 hours before the solid precipitate was filtered and dried in air to obtain shiny light pink crystalline solid of analytically pure Complex 2, as shown in Scheme 2 (yield 3.93 g; 95% based on $Co(ClO_4 6H_2O;)$); mp 180° C. dec. Anal. Calcd. for $C_{16}H_{30}N_8ClO_4P_2S_2CO$: C, 31.04; H, 4.85; N, 18.11; Cl, 573. Found: C, 31.02; H, 4.87; N, 18.10; Cl. 575.

Synthesis of Complex 3 (Scheme 2): To a solution of 1 (4.53 g: 19.70 mmol) in THF (150 mL) was added dropwise (30 minutes) with stirring at 0° C. a solution of $Cu(clO_4)_2 6H_2O$ (1.82 g; 4.92 mmol) in absolute ethanol (50 mL). The mixture on stirring at 25° C. for 8 hours turned greenish with suspensions of similar colored solid precipitate. The solvents were removed under vacuo and the crystalline residue was washed successively (4×25 mL) the THF to remove the unreacted excess of 1. The leftover green solid was found to be analytically pure Complex 3, as shown in Scheme 2 (yield 2.80 g; 91% based on $Cu(ClO_4)_2 6H_2O$ ); mp 194 C. dec. Anal. Calcd for C, 30.81; H, 4.81; N, 17.97; Cl, 5.69. Found: C,30.84; H, 4.83; N, 17.96; Cl, 5.71.

Synthesis of Complex 4 (Equation 1): A solution of $PdCl_2(PhCN)_2$ (3.53 g; 9.22 mmol) in $CH_2Cl_2$ (100 mL) was added dropwise (15 minutes) at 25° C. to a solution of i (2.12 g; 9.22 mmol) also in $CH_2Cl_2$ (100 ml). The dark orange colored mixture on stirring for 4 hours turned yellow and the solvent was removed in vacuo to obtain a brown colored microcrystalline solid which upon washing with THF (2×10 ml) gave analytically pure Complex 4, as shown in Equation 1 (yield 3.42 g; 91%) mp 210° C. dec. Anal. calcd. for $C_8H_{15}N_4Cl_2PSPd$: C, 23.56; H, 3.68; N, 13.74; cl, 17.40. Found: C,23.54; H, 3.70; N, 13.71; Cl, 17.51.

Synthesis of Compound 5 (Scheme 3): To a solution of 1 (3.50 g; 15.26 mmol) in absolute ethanol (100 ml) was added dropwise (15 minutes) at 25° C. with stirring a solution of salicyladehyde (3.81 g; 31.28 mmol) in absolute ethanol (100 ml). The mixture was stirred under reflux for 12 hours before the solvent was removed under vacuo to obtain a white crystalline sold of Compound 5 (Scheme 3) which was recrystallized from boiling acetonitrile (yield 6.4 g; 96%); mp 80° C. Anal. Calcd for $C_{22}H_{23}N_4O_2PS$: C, 60.22; H, 5.25; N, 12.78. Found C,60.21; H, 5.21; N, 12.74.

Synthesis of Compound 6 (Scheme 3): Was synthesized by the reaction of 1 with piperazine aldehyde (Scheme 3) under identical reaction conditions as described above for Recrystallization from CH$_3$CH/CHl$_3$ (3:1) (yield 88%) mp 109° C. Anal. Calcd for C$_{18}$H$_{31}$N$_8$PS: C, 51.11; H, 7.34; N, 26.52. Found: C, 51.14; H, 7.37; N, 26.50.

Synthesis of Complex 7 (Scheme 4): To a solution of 5 (2.95 g; 6.73 mmol) in THF (100 mL) was added with stirring at 25° C. a solution of PdCl$_2$(PhCN)$_2$ (2.58 g; 6.73 mmol) also was removed under vacuo to obtain a brown microcrystalline solid of 7 (Scheme 4). The crude 7 was washed with chilled CH$_2$Cl$_2$(2×10 mL) to remove the residual benzonitrile before it was recrystallized from acetonitrile (yield 3.60 g; 92%); mp 151° C. (dec). Anal. Calcd for C$_{22}$H$_{22}$N$_4$ClO$_2$PSPd: C, 45.64; H, 3.83; N, 9.67; Cl, 6.12. Found: C, 45.57; H, 3.84; N, 9.70; Cl, 6.10.

Synthesis of Complex 8 (Scheme 4): to a suspension of 6 (2.75 g; 6.51 mmol) in dichloromethane (50 mL) was added with stirring at 25° C. a solution of Pdcl$_2$(PhCN)$_2$ (2.49 g; 6.51 mmol) also in dichloromethane (50 mL). The mixture was stirred for 6 hours before the solvent was removed in vacuo to obtain an orange colored microcrystalline solid of 8 (Scheme 4). Recrystallization from boiling CH$_3$CN gave analytically pure 8 (yield 3.25 g; 83%); mp. 163° C.(dec). Anal. Calcd for C$_{18}$H$_{31}$N$_8$Cl$_2$PSPd: C, 36.02; H, 5.17; N, 18.67; Cl, 11.82. Found: C, 36.11; H, 5.15; N, 18.63; Cl, 11.84.

EXAMPLE III

SYNTHESIS OF MONO-PHOSPHORUS HYDRAZIDES AND THEIR Pd(II) COMPLEXES

Synthesis of Phosphorohydrazidothioic acid, 1-methyl-, 0,0-dimethyl ester, Phosphorohydrazidothioic acid, 1-methyl-, 0,0-diethyl ester, Phosphorohydrazidic acid, N1-methyl-, diphenyl ester Phosphorohydrazidic acid, N1-methyl-, 0,0-diphenyl.

A solution of methyl hydrazine (75 mmol) in CHCl$_3$ (75 mL) was added dropwise to a solution of the respective phosphorus chloride (30 mmol) also in 75 mL of CHCl$_3$ maintained at 0° C. The reaction mixture was stirred for 6 hours at 25° C. before the methyl hydrazine hydrochloride adduct was filtered off and the filtrate evaporated to dryness in vacuo. (CH$_3$O)$_2$P(S)NMeNH$_2$ yielded a mixture of products and required separation by flash chromatography. This was achieved by using silica Gel 60 as the stationary phase and a solvent system comprised of hexane:ethyl acetate::methanol in the ratio 9:3:1. The other compounds were recrystallized in CH$_3$CN to obtain the pure monophosphorus hydrazides.

(CH$_3$O)$_2$P(S)NMeNH$_2$ oil, yield 80% MS (M$^+$) 170; $^{31}$P NMR (CDCl$_3$): 81.5 (s) . $^1$H NMR (CDCl$_3$): 3.72 (d, 13.5 Hz, 6H, P—(OC$\underline{H}_3$)); 2.94 (d, 10.8 Hz, N—CH$_3$); 3.61 (s, 2H, NH$_2$). Anal. Calcd. for C$_3$H$_{11}$N$_2$O$_2$PS: C, 21.12; H, 6.52; N, 16.47. Found: C, 21.09; H, 6.51; N, 16.45.

(C$_2$H$_5$O)$_2$P(S)NMeNH$_2$ oil, yield 91%. $^{31}$P NMR (CDCl$_3$): 77.88 (s). $^1$H NMR (CDCl$_3$): 1.18 (t, 6H, P—OCH$_2$C$\underline{H}_3$); 2.78 (d, 8.1 Hz, 3H, N—CH$_3$); 3.47 (s, 2H, NH$_2$); 3.97 (m, 4H, P—OC$\underline{H}_2$CH$_3$). Anal. Calcd. for C$_5$H$_{15}$N$_2$O$_2$PS: C, 30.30; H, 7.63; N, 14.14. Found: C, 30.29; H, 7.62; N, 14.13.

(C$_6$H$_5$O)$_2$P(O)NMeNH$_2$ yellow powder, Yield 89%, mp 41° C. $^{31}$P NMR (CDCl$_3$): 0.294, $^1$H NMR (CDCl$_3$): 2.87 (d, 7.8 Hz, 3H, N—CH$_3$); 3.52 (s, 2H, NH$_2$); 7.1–7.4 (m, 10H, (OPh)). Anal. Calcd. for C$_{13}$H$_{15}$N$_2$O$_3$P: C, 56.11; H, 5.43; N, 10.07. Found: C, 56.09; H, 5.42; N, 10.05.

(C$_6$H$_5$)$_2$P(O)NMeNH$_2$ white powder, yield 90%, mp 121° C. $^{31}$P NMR (CDCl$_3$): 29.2, $^1$H NMR (CDCl$_3$): 2.62 (d, 8.7 Hz, 3H, N—CH$_3$); 3.48 (s, 2H, NH$_2$); 7.5–7.9 (m, 10H, —(Ph)). Anal. Calcd. for C$_{13}$H$_{15}$N$_2$OP: C, 63.41; H, 6.14; N, 11.38. Found: C, 63.40; H, 6.13; N, 11.36.

Synthesis of Compounds R$_2$P(E)NMeNH$_2$.PdCl$_2$ (R=OCH$_3$, E=S, R=OC$_2$H$_5$, E=S, R=OC$_6$H$_5$, E=O, R=C$_6$H$_5$, E=O.

To a sample of the monophosphorus hydrazide (1 mmol) in CH$_2$Cl$_2$ (25 mL) was added dropwise with stirring at 25° C. a solution of PdCl$_2$ (PhCN)$_2$ (1 mmol) also in CH$_2$Cl$_2$ (25 mL). An orange colored precipitate slowly appeared. The mixture was stirred for 2 hours before the precipitate was filtered off and washed first with hexane (3×10 mL) and then with diethyl ether (×10 mL). The micro-crystalline solid compounds 5–8 (Schemes 5–6) were then recrystallized from boiling acetonitrile.

(CH$_3$O)$_2$P(S)NMeNH$_2$.PdCl$_2$ brown crystals; yield 89%; mp<118° C. dec. $^{31}$P NMR (CDCl$_3$): 87.5. $^1$H NMR (CDCl$_3$): 3.87 (d, 14.1, 6H, P—(OC$\underline{H}_3$)); 3.12 (d, 9.3 Hz, 3H, N—CH$_3$). Anal. Calcd. for C$_3$H$_{11}$N$_2$O$_2$PSPdCl$_2$: C, 10.37; H, 3.19; N, 8.06; Cl, 20.41. Found: C, 10.35; H, 3.16; N, 8.05; Cl, 20.40.

(C$_2$H$_5$O)$_2$P(S)NMeNH$_2$. PdCl$_2$ brown powder; yield 90%; mp; <100° C. dec $^{31}$P NMR (CDCl$_3$): 83.5. $^1$H NMR (CDCl$_3$): 1.29 (t, 6H, P—OCH$_2$C$\underline{H}_3$); 3.24 (d, 9.4 Hz, 3H, N—CH$_3$); 4.41 (m, 4H, P—OC$\underline{H}_2$CH$_3$). Anal. Calcd. for C$_5$H$_{15}$N$_2$O$_2$PSPdCl$_2$: C, 15.99; H, 4.03; N, 7.46; Cl, 18.88. Found: C, 15.97; H, 4.01; N, 7.45; Cl, 18.87.

(C$_6$H$_5$O)$_2$P(O)NMeNH$_2$. PdCl$_2$ brown powder; yield 85%; mp<138° C. dec. $^{31}$P NMR (CDCl$_3$): —4.01. $^1$H NMR (CDCl$_3$); 2.7 (d, 12.6 Hz, 3H, N—CH$_3$); 7.1–7.6 (m, 10H, —(OPh)). Anal. Calcd. for C$_{13}$H$_{15}$N$_2$O$_3$PPdCl$_2$: C, 34.27; H, 3.32; N, 6.15; Cl, 15.56. Found: C, 34.25; H, 3.30; N, 6.13; Cl, 15.55.

(C$_6$H$_5$)$_2$P(O)NMeNH$_2$. PdCl$_2$ brown powder; yield 87%; mp<141° C. dec. $^{31}$P NMR (CDCl$_3$): 25.91. $^1$H NMR (CDCl$_3$): 2.56 (d, 11.1 Hz, 3H, N—CH$_3$); 7.4–7.8 (m, 10H, —(Ph)). Anal. Calcd. for C$_{13}$H$_{15}$N$_2$POPdCl$_2$: C, 36.86; H, 3.57; N, 6.61; Cl, 16.74. Found: C, 36.85; H, 3.56; N, 6.57; Cl, 16.73.

Synthesis of C$_6$H$_5$P(S)(NMeNH$_2$(NMeNCHC$_6$H$_4$COOH) (Scheme 5)

A solution of 4-carboxybenzaldehyde (1.3 g, 8.7 mmol) in ethanol (50 mL) was added dropwise to an ethanolic solution (100 mL) of phosphorus bis (hydrazide) sulfide C$_6$H$_5$(S)(NMeNH$_2$)$_2$ (1 g, 8.7 mmol) which had been cooled to −70° C. The solution was allowed to warm to 25° C. and stirred for an additional 4 h. The thin layer chromatographic analysis of the solution showed three spots (Rf=0.3, 0.6 and 0.9). The solvent was removed in vacuo to obtain a white powdery residue. The three components were separated by flash chromatography (silica gel) with a solvent system of hexane:ethyl acetate: MeOH in the ratio of 6:4: 1. The eluants of each of the fractions were combined and evaporated to give the components as white crystalline powders. The component which showed an Rf of 0.6 was identified to be the mono-carboxylate derivative C$_6$H$_5$P(S) (NMeNH$_2$(NMeNCHC$_6$H$_4$COOH) whereas, the component of Rf of 0.3 was the biscarboxylate compound C$_6$H$_5$P(S) (NMeNH$_2$(NMeNCHC$_6$H$_4$COOH)$_2$. The starting compound 1 (Scheme 5) showed an Rf of 0.9.

C$_6$H$_5$P(S) (NMeNH$_2$) (NMeNCHC$_6$H$_4$COOH), white powder; yield 73%; mp, 97° C. $^{31}$P NMR (CDCl$_3$): 82.34. $^1$H NMR (CDCl$_3$): 2.9 (d, 3H, $^3J_{P\text{-}H}$=12.1 Hz), 2.41 (d, 3H, $^3J_{P\text{-}H}$=14.1 Hz), 7.57 (s, 1H, N=CH), 7.39–8.09 (m, 9H, aromatic protons). $^{13}$C NMR (CDCl$_3$): 40.16 (d, $^2J_{P-C}$=15.1 Hz), 31.99 (d, $^2J_{P-C}$=9.8 Hz), 143.1 (s, NC=H), 140.28, 136.58, 132.70, 132.34, 130.57, 130.31, 129.47, 128.28, 127.94, 126.31 (aromatic carbons). IR (KBr): 3216 (NH$_2$); 1670 (C=O); 603 (P=S). Anal. Calcd. for C$_{16}$H$_{19}$N$_4$O$_2$PS: C, 53.03; H, 5.28; N, 15.46. Found: C, 53.44; H, 5.45; N, 15.31. 3: (Scheme 5) Yield 12%; white powder; mp 103° C. Anal Calcd for C$_{24}$H$_{23}$N$_4$O$_4$PS: C, 58.29; H, 4.69; N, 11.33. Found, C, 58.35; H, 4.71; N, 11.30.

C$_6$H$_5$P(S) (NMeNH$_2$)$_2$ was recovered in 12% yield.
Synthesis of C$_6$H$_5$P(S) (NMeNCHC$_6$H$_4$COOH)$_2$ (Scheme 5)

A solution of 4-carboxybenzaldehyde (2.69 g, 17.4 mmol) in THF (50 mL) was added dropwise at 25° C. to a THF solution (100 mL) of C$_6$H$_5$P(S) (NMeNH$_2$)$_2$ (2 g, 8.7 mmol). The mixture was stirred at RT for 6 h before the solvent was removed in vacuo to obtain a white crystalline powder of 3 (Scheme 5). The final purification of 3 was achieved by boiling the solid in acetonitrile and cooling the solution to 0° to produce pure 3 (yield 89%), mp 103° C. Anal Calcd for C$_{24}$H$_{23}$N$_4$O$_4$PS: C, 58.29; H, 4.69; N, 11.33. Found, C, 58.31; H, 4.67; N, 11.29.$^{31}$P NMR (CDCl$_3$): 80.04. $^1$H NMR (CDCl$_3$): 3.21 (d, 6H, $^3J_{P-H}$=12.3 HZ), 7.67 (s, 2H, N=CH), 7.35–7.97. (m, 13H, aromatic protons). IR (KBr): 1647 (C=O); 605 (P=S).$^{13}$C NMR (DMSO): 33.14 (d, $^2J_{P-C}$=9.75 Hz), 139.39 (s, NC=H), 171.7 (s, COOH), 126.07, 127.6, 127.7, 128.2, 129.8, 130.6, 130.9, 131.9, 133.1, 133.2, 136.4, 136.6 (aromatic carbons).
Synthesis of C$_6$H$_5$P(S)(NMeNH$_2$(NMeCHC$_6$H$_4$CH=CH—COOH)

To a methylene chloride (100 mL) solution of C$_6$H$_5$P(S) (NMeNH$_2$)$_2$ (4.60 g; 20.0 mmol) was added dropwise at 0° C. a solution of 4-formylcinnamic acid (3.50 g; 19.9 mmol) also in methylene chloride (100 mL). The mixture was allowed to warm to 25° C. and stirred for 6 hours before the solvent removed in vacuo to obtain a yellow powder. Unreacted C$_6$H$_5$P(S) (NMeNH$_2$)$_2$ and the bis—cinnamic acid adduct C$_6$H$_5$P(S) (NMeNCHC$_6$H$_4$—(H=HCOOH)$_2$ were removed by washing the yellow powder with diethyl ether (2×25 mL). Recrystallization with dry acetonitrile gave pure 4 (89%) (Scheme 5), mp 68° C. Anal Calcd for C$_{18}$H$_{21}$N$_4$O$_2$PS: C, 55.66; H, 5.45; N, 14.43. Found: C, 55.37; H, 5.41; N, 14.37. $^{31}$P NMR (DMSO): 81.37. $^1$H NMR (DMSO): 2.82 (d, 3H, $^3J_{P-H}$=11.2 Hz), 3.4 (d, 3H, $^3J_{P-H}$=12.2 Hz), 7.34 (s, 1H, N=CH), 5.5–8.3 (m, 11H, aromatic and HC=CH protons) $^{13}$C NMR (CH$_3$OD): 32.16 (d, $^3J_{P-C}$=10.1 Hz), 40.97 (d, $^3J_{P-C}$=14.98 Hz), 146.37 (s, N C=H), 170.31 (s, COOH), 119.64, 121.51 (>C=C<), 139.21, 139.13, 183.77, 138.68, 138.19, 138.09, 136.07, 135.92, 134.44, 134.36, 133.99, 133.92, 133.01, 132.93, 129.71, 129.53, 129.37, 129.09, 128.99, 128.80, 128.69, 128.02, 127.99. IR (KBr): 3179 (NH$_2$); 1671 (C=N); 608 (P=S); 1650 (c=O).
Synthesis of Pd(II) Complexes of C$_6$H$_5$P(S) (NMeNH$_2$) (NMeNCHC$_6$H$_4$COOH), C$_6$H$_5$P(S) (NMeNCHC$_6$H$_4$COOH)$_2$, and C$_6$H$_5$P(S) (NMeNH$_2$) (NMeNCHC$_6$H$_4$—(H=CH—COOH) (Scheme 6).

A solution of PdCl$_2$(PhCN)$_2$ (637 mg, 1.66 mmoles) in CH$_2$Cl$_2$ (25 mL) was added dropwise at 25° C. to a CH$_2$Cl$_2$ solution of C$_6$H$_5$P(S) (NMeNH$_2$) (NMeNCHC$_6$H$_4$COOH) (600 mg, 1.66 mmoles). The reaction mixture was stirred for 2 hours before the solvent removed in vacuo to obtain an orange solid C$_6$H$_5$P(S) (NMeNH$_2$) (NMeNCHC$_6$H$_4$COOH). PdCl$_2$ which was repeatedly washed with dry hexane to remove the benzonitrile byproduct. Final purification of 6 was achieved through crystallization in acetonitrile (yield 73%), mp 134° C. (dec) Anal Calcd for C$_{16}$H$_{19}$N$_4$O$_2$PSPdCl$_2$: C, 35.68; H, 3.55; N, 10.40; Cl, 13.14. Found: C, 35.62; H, 3.61; N, 9.99, Cl, 13.01. $^{31}$P NMR (DMSO): 84.38.$^1$H NMR (DMSO): 2.43 (d, 3H, $^3J_{P-H}$=11.8 HZ), 3.24 (d, 3H, $^3J_{P-H}$=12.4 HZ), 7.61 (s, 1H, N=CH), 7.4–8.88 (m, 9H, aromatic protons). IR (KBr): 1673 (C=O); 3245 (NH$_2$); 553 (P=S).

The Pd(II) complexes of C$_6$H$_5$P(S) (NMeNH$_2$) (NMeNCHC$_6$H$_4$COOH)$_2$ and C$_6$H$_5$P(S) (NMeNH$_2$) (NMeNCHC$_6$H$_4$—CH=CHCOOH) were prepared following the procedure as described above by the interaction of the respective carboxylate functionalized phosphorus hydrazides with PdCl$_2$ (PhCN)$_2$ in dichloromethane. Purification of the crude complexes C$_6$H$_5$P(S) (NMeNH$_2$) (NMeNCHC$_6$H$_4$COOH)$_2$. PdCl$_2$ and C$_6$H$_5$P(S) (NMeNH$_2$) (NMeNCHC$_6$H$_4$CH=CH—COOH). PdCl$_2$ was effected through recrystallization in acetonitrile.

C$_6$H$_5$P(S) (NMeNH$_2$) (NMeNCHC$_6$H$_4$COOH)$_2$. PdCl$_2$ orange red crystals (75%), mp 195° C. (dec). Anal Calcd for C$_{24}$H$_{23}$N$_4$O$_4$PSPdCl$_2$: C, 42.99; H, 3.46; N, 8.36; Cl, 10.55. Found: C, 42.87; H, 3.45; N, 8.37, Cl, 10.13. $^{31}$P NMR (DMSO): 82.79. $^1$H NMR (DMSO): 3.25 (d, 3H, $^3J_{P-H}$=11.3 Hz), 3.61 (d, 3H, $^3J_{P-H}$=10.8 Hz), 8.81 (s, 1H, N=CH), 7.71 (s, 1H, N=CH), 7.4–8.9 (m, 13H, aromatic protons). IR (KBr): 1651 (C=O); 555 (P=S).

C$_6$H$_5$P(S) (NMeNH$_2$) (NMeNCHC$_6$H$_4$CH=CH—COOH). PdCl$_2$ brown cubic crystals (69%), mp 168° C. (dec). Anal Calcd for C$_{18}$H$_{21}$N$_4$O$_2$PSPdCl$_2$: 38.22; H, 3.74; N, 9.91; Cl, 12.54. Found: C, 38.71; H, 3.75; N, 9.87; Cl, 12.23. $^{31}$P NMR (DMSO): 83.62. $^1$H NMR (DMSO): 2.86 (d, 3H, $^3J_{P-H}$=11.0 Hz), 3.64 (d, 3H, $^3J_{P-H}$=12.1 Hz), 7.43 (s, 1H, N=CH),5–8.2 (m, 11H, aromatic and C=C protons). IR (KBr): 1647 (C=O); 3193 (NH$_2$); 557 (P=S).
Conjugation of C$_6$H$_5$P(S) (NMeNH$_2$) (NMeNCHC$_6$H$_4$COOH) to n-butylamine (Scheme 7)

To 500 mg of C$_6$H$_5$P(S) (NMeNH$_2$)(NMeNCHC$_6$H$_4$COOH ) (1.38 mmoles) in 30 mL of methylene chloride was added 139 mg (1.38 mmoles) of triethylamine. The mixture was stirred for 10 minutes after which 188 mg (1.38 mmoles) of isobutyl chloroformate was added. The reaction mixture was stirred for 30 minutes, after which 125 mg (1.38 mmoles) of n-butylamine was added dropwise in a solution of methylene chloride. Evaporation under reduced pressure gave a brown precipitate, which was extracted in chloroform and washed with brine and subsequently dried over MgSO$_4$. The brownish precipitate obtained was passed through celite to yield the pure n-butyl amine conjugated product 9 (Scheme 7). Yield 69%; brown powder. $^{31}$P NMR (CDCl$_3$); 85.07 ppm. $^1$H NMR (CDCl$_3$); δ2.65 (d, 3H, NCH$_3$); 3.25 (d, 3H, NCH$_3$); 6.6–8.5 (m, ar. and imine H); 0.97 (m, 3H, CH$_3$); 1.38 (m, 4H, CH$_2$—CH$_2$—); 1.58 (m, 2H, —HN—CH$_2$). IR (KBr): 3195 (NH$_2$); 1648 (C=O); 557 (P=S). Anal. Calcd. for C$_{20}$H$_{28}$N$_5$Cl$_2$OPSPd: C, 40.39; H, 4.74; N, 11.78; Cl, 11.92. Found: C, 39.31; H, 4.07; N, 11.53; Cl, 11.76.

The invention has been described in an illustrative manner, and it is to be understood that the terminology which has been used is intended to be in the nature of words of description rather than of limitation.

Throughout this application various publications are referenced by full citation or numbers. Full citations for the publications referenced by number are listed below. The disclosures of these publications in their entireties are hereby incorporated by reference into this application in order to more fully describe the state of the art to which this invention pertains.

Obviously many modifications and variations of the present invention are possible in light of the above teachings. It is, therefore, to be understood that within the scope of the appended claims, the invention may be practiced otherwise than as specifically described.
EQUATION 1
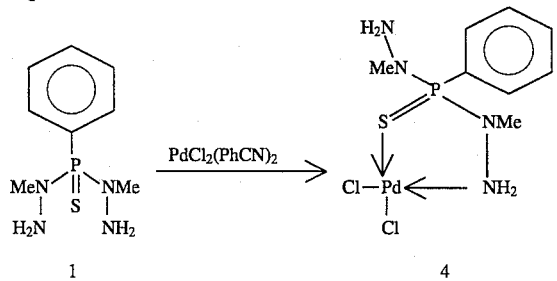
SCHEME 2
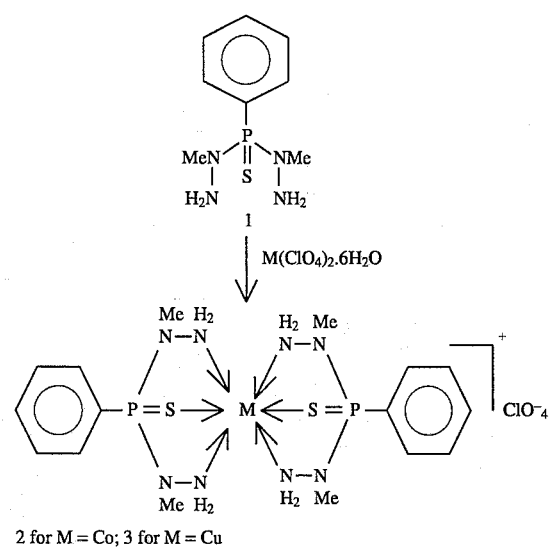
2 for M = Co; 3 for M = Cu
Scheme 3
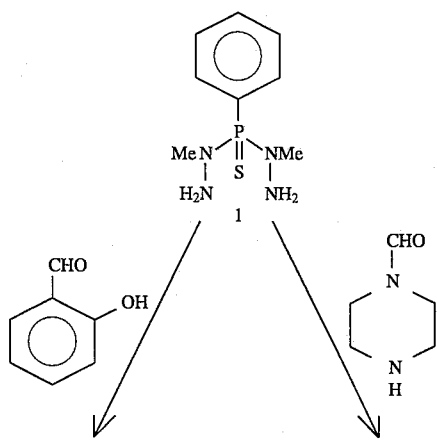
-continued
Scheme 3
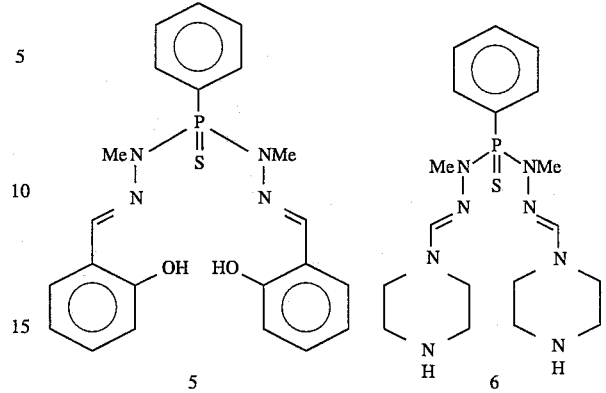
Scheme 4
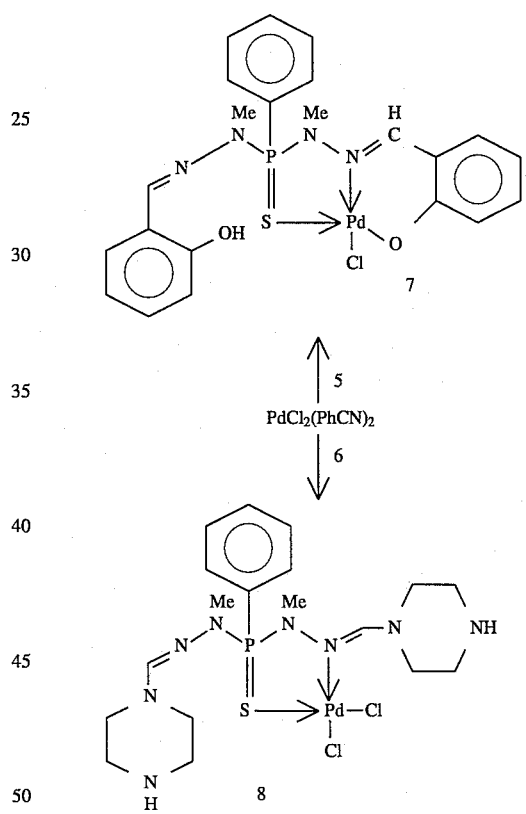
SCHEME 5
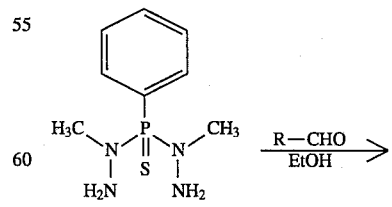

17
-continued
SCHEME 5
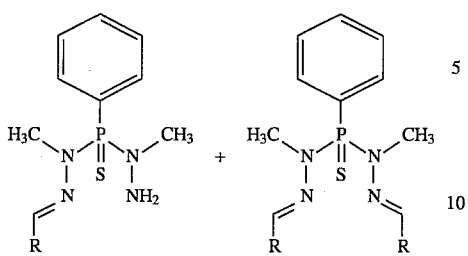
R = C₆H₄COOH    2
R = C₆H₄CH=CHCOOH    4
    3
    5
SCHEME 6
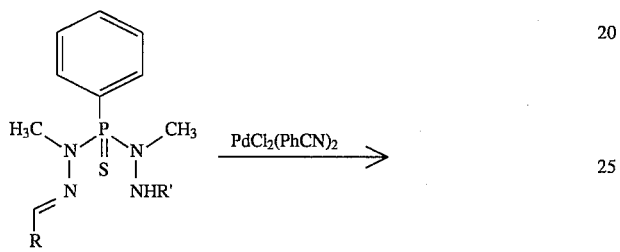
18
-continued
SCHEME 6
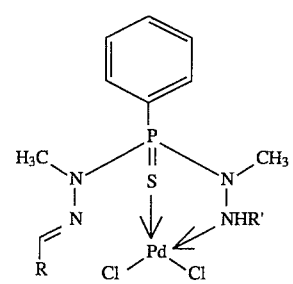
R = C₆H₄COOH, R' = H, 6
R, R' = C₆H₄COOH, 7
R = C₆H₄CH=CHCOOH, R' = H, 8
SCHEME 7
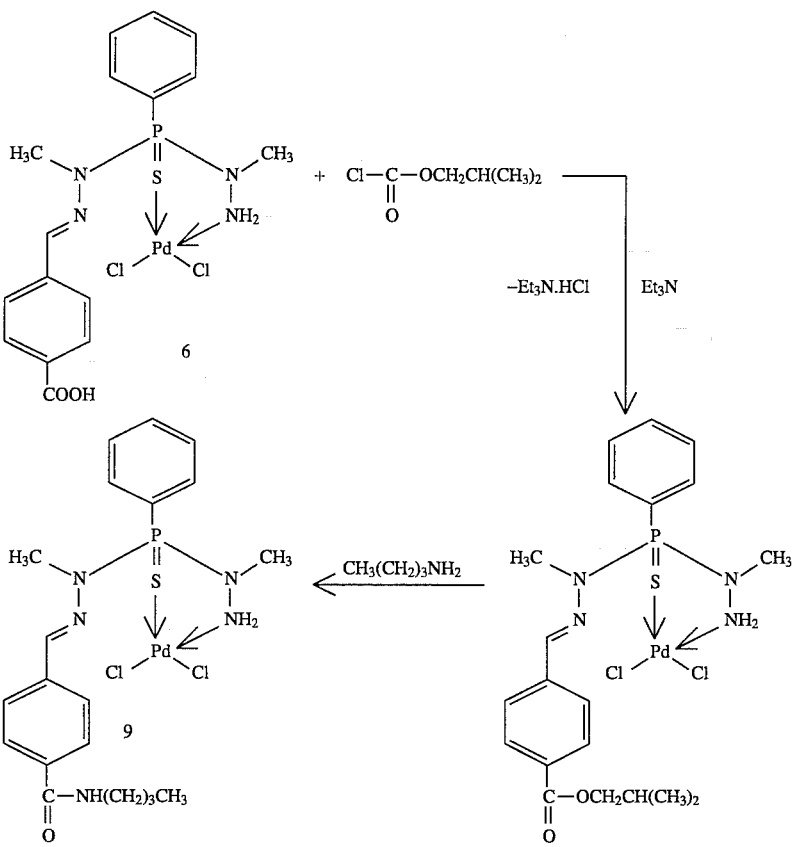

REFERENCES

Abrams et al., "Synthesis and crystal and molecular structure of a Technetium-Hydralazino complex . . ." *Inorg Chim Acta* 173:133–135, 1990a.

Abrams et al., "Technetium-99m-human polyclonal IgG radiolabeled via the Hydrazino Nicotinamide derivative for imaging focal sites of infection in rats" *J Nucl Med* 31:2022–2028, 1990b.

Andres et al., Radionuclides for therapy: a review. In: *Radionuclides for Therapy*, edited by Schubiger, P. and Hasler, P. Basle, Switzerland: Editones-Roches, p. 9–20, 1986.

Deshpande et al., "$^{90}$Y-labeled monoclonal antibody for therapy; labeling by a new macrocyclic bifunctional chelating agent" *N Nucl Med* 31:473–479, 1990.

Dewanjee, "The chemistry of $^{99m}$Tc-labeled radiopharmaceuticals" *Sem Nucl Med* 20:5–27, 1990.

Hnatowich, "Antibody radiolabeling, problems and promises" *Nucl Med Bio Int J Radiat Appl Inst [B]* 17:49–55, 1990.

Kozak et al., "Nature of bifunctional chelating agent used for radioimmunotherapy with $^{90}$Y monoclonal antibodies: Critical factors in determining in vivo survival and organ toxicity" *Cancer Res* 39:2639–2644, 1989.

Kung et al., "Current and future radiopharmaceuticals for brain imaging with single photon emission computed tomography" *Sem Nucl Med* 20:290–302, 1990.

Mausner et al., Production and use of prospective radionuclides for radioimmunotherapy. In: *Radiolabled monoclonal antibodies for imaging and therapy*, edited by Srivastava, S.C. New York: Plenum Publishing Corp., p. 149–163, 1988.

Meares et al., "Chelate radiochemistry: Clearable linkers lead to altered levels of radioactivity in the liver" *Int J Cancer* 2:99–102, 1988.

Naruki et al., "Differential cellular catabolism of $^{111}$In, $^{90}$Y and $^{125}$I radiolabeled T101 Anti-CD5 monoclonal antibody" *Nucl Med Biol; Int J Radiat Appl Inst [B]* 17:201–207, 1990.

Parker, "Tumour targeting with radiolabelled macrocycle-Antibody conjugates" *Chem Soc Rev* 19:271–291, 1990.

Rao et al., "Dependence of immunoreactivity and tumor uptake on ratio of Tc and Re N$_2$S$_2$complexes per antibody F$_{ab}$ fragment" *J nucl Med* 29:815, 1988.

Saenger et al., "Radiotherapeutic agents: properties, dosimetry and radiobiologic considerations" *Semin Nucl Med* 9:72–84, 1979.

Schlom, "Basis principles and applications of monoclonal antibodies in the management of carcinomas" *Canc Res* 46:3225–3238, 1986.

Schubiger and Hasler, *Radionuclides for therapy*, Basel, Switzerland: Hoffman-LaRoche & Co., Ltd., 1986.

Spencer et al., *Radionuclides in therapy*, Boca Raton, FL: CRC Press, 1987.

Volkert et al., "Therapeutic Radionuclides: Production and decay property considerations" *J Nucl Med* 32:1991.

Washburn et al., "p-NH$_2$-Bz-DOTA-3A, a new bifunctional chelate reagent for labeling monoclonal antibodies with $^{90}$Y" *J Nucl Med* 31:824, 1990.

What is claimed is:

1. A compound for use as a diagnostic or therapeutic pharmaceutical, or MRI contrast agent, said compound comprising:

a phosphine core, and two hydrazine groups forming a ligand bound to a transition metal extending from said phosphorous core wherein said ligand is of the formula

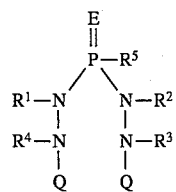

wherein $R^1$, $R^2$, $R^3$, $R^4$ are all the same or different and are H, an alkyl group selected from Me, Et, n- or i-propyl, n-, i- or t-butyl, n-hexyl, —CH$_2$COOH, —CH(OH)CH$_2$OH), cyclohexyl, an alkylamine group selected from —NMe$_2$, NHMe, (CH$_2$)$_n$NMe$_2$, (CH$_2$)$_n$NHMe, —(CH$_2$)$_n$NH$_2$, an alkoxy group selected from —O(CH$_2$)$_n$CH$_3$, (CH$_2$)$_n$OCH$_3$, —(CH$_2$)$_n$—COOH, —(CH$_2$)$_n$SH, an aromatic group of the formula —C$_6$H$_4$R wherein R=H, NH$_2$, COOH, OH, NCS, CHO, activated esters, acid anhydrides, N-hydroxy succinamide, and SiMe$_3$;

$R^5$ is H, OCH$_3$—CH(OH)—CH$_2$OH, Me or Ph E is O or S; Q is H, —CH$_2$Ph or —CHPh wherein in each instance Ph is unsubstituted or substituted with OH, COOH, O alkyl wherein alkyl are from 1 to 4 carbon atoms, NH$_2$, NH(alkyl C$_{1-4}$) or NH(alkyl C$_{1-4}$)$_2$, or halogen such as chlorine, fluorine, bromine or iodine or Q can be —CH$_2$ piperazino or —CH piperazino; and wherein when $R^5$ is Ph, $R^1$, $R^2$, $R^3$, and $R^4$ are not methyl or ethyl and wherein when $R^5$ is Ph, E is O, and Q is H, then $R^3$ and $R^4$ are not phenyl.

2. A compound as set forth in claim 1 wherein said metal is a metallic isotope selected form the group including γ and β emitting isotopes, said compound being stable in aqueous solutions, serum and other body fluids.

3. The compound as set forth in claim 2 wherein said metallic isotope is a radionuclide selected from the group including $^{186}$Re, $^{188}$Re, $^{109}$Pd, $^{105}$Rh and $^{99m}$Tc, said compound being stable in aqueous solutions, serum and other body fluids.

4. A compound as set forth in claim 1 wherein any one or several of $R^1$, $R^2$, $R^3$, $R^4$, $R^5$, or $R^6$ or are benzyl isocyanate, bromacetamide, an activated ester, N-hydroxysuccinimides, a cleavable ester or an aldehyde.

5. A compound as set forth in claim 1 wherein any one or all of $R^1$, $R^2$, $R^3$, $R^4$, $R^5$, or $R^6$ are carboxylated or hydroxylated to render said ligand more polar.

6. A compound for use as a diagnostic, therapeutic pharmaceutical, or MRI contrast agent of the formula

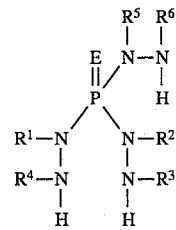

forming a ligand bound to a transition metal wherein $R^1$, $R^2$, $R^3$, $R^4$ are all the same or different and are H, an alkyl group selected from (Me, Et, n- or i-propyl, n-, i- or t-butyl, or n-hexyl, cyclohexyl, an alkylamine group selected from —NMe$_2$, NHMe, (CH$_2$)$_n$NMe$_2$, (CH$_2$)$_n$NHMe, —(CH$_2$)$_n$NH$_2$, an alkoxy group selected from —O(CH$_2$)$_n$CH$_3$, (CH$_2$)$_n$OCH$_3$, an aromatic of formula —C$_6$H$_4$R wherein R=H, NH$_2$, COOH, NCS, CHO, activated esters, acid anhydrides, N-hydroxy succinamide, and SiMe$_3$);

R$^5$, R$^6$ are all the same or different and are H, Me or Ph; E is O or S.

7. A compound as set forth in claim 6 wherein any one or several of R$^1$, R$^2$, R$^3$, R$^4$, R$^5$ or R$^6$ or are benzyl isocyanate, bromacetamide, an activated ester, N-hydroxysuccinimides, a cleavable ester or an aldehyde.

8. A compound as set forth in claim 6 wherein any one or all of R$^1$, R$^2$, R$^3$, R$^4$, R$^5$, or R$^6$ are carboxylated or hydroxylated to render said ligand more polar.

9. A compound for use as a diagnostic, therapeutic pharmaceutical, or MRI contrast agent selected from the group consisting of the formulas

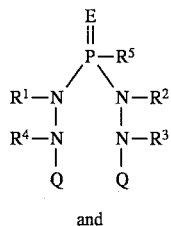

and

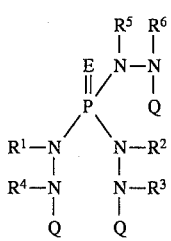

forming a ligrand bound to a transition metal wherein E is O or S;

wherein R$^5$ is H, —OCH$_3$, —CH(OH)—CH$_2$OH, CH$_3$, Ph;

wherein R$^1$, R$^2$, R$^3$, R$^4$ and R$^6$ are the same or different and are H, cyclohexyl, —CH$_2$COOH, —CH(OH)CH$_2$OH, an alkyl group of formula (C$_{0-6}$)NYZ wherein each of Y and Z is hydrogen or lower alkyl C$_1$-C$_4$, straight or branched alkoxy having from 1 to 6 carbon atoms, —(CH$_2$)$_n$—OCH$_3$ wherein $n$ is 1 to 6, phenyl or phenyl substituted with OH, NH$_2$, COOH, NCS, CHO, activated esters, acid anhydrides, N-hydroxysuccinamide, SiMe$_3$;

Q is H, —CH$_2$Ph or —CHPh wherein each Ph is unsubstituted or substituted with OH, COOH, alkyl wherein alkyl has from 1 to 4 carbon atoms, alkyl (C$_{0-6}$)NYZ wherein Y and Z are as defined above or Ph is substituted with halogen, or Q is —CH$_2$ piperazino or =CH piperazino; and wherein when the ligand is the dihydrazine E, is O, Q is H, and R$^5$ is Ph, then R$^4$ and R$^4$ are not Ph.

10. A compound for use as a diagnostic or therapeutic pharmaceutical, or MRI contrast agent, said compound comprising: a phosphine core, and at least two hydrazine groups forming a bis-hydrazine phosphine ligand bound to a transition metal extending from said phosphorous core of the formula

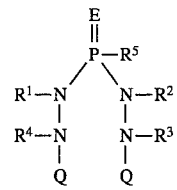

wherein R$^1$, R$^2$, R$^3$, R$^4$ are all the same or different and are H, an alkyl group selected from Me, Et, n- or i-propyl, n-, i- or t-butyl, n- hexyl, —CH$_2$COOH, —CH(OH)CH$_2$OH), cyclohexyl, an alkylamine selected from —NMe$_2$, NHMe, (CH$_2$)$_n$NMe$_2$, (CH$_2$)$_n$NHMe, —(CH$_2$)$_n$NH$_2$, an alkoxy group selected from —O(CH$_2$)$_n$CH$_3$, (CH$_2$)$_n$OCH$_3$, —(CH$_2$)$_n$—COOH or —(CH$_2$)$_n$SH, an aromatic of formula (—C$_6$H$_4$R wherein R=H, NH$_2$, COOH, OH, NCS, CHO, activated esters, acid anhydrides, N-hydroxy succinamide, and SiMe$_3$);

R$^5$ is H, OCH$_3$—CH(OH)—CH$_2$OH, Me or Ph;

E is O or S; Q is H, —CH$_2$Ph or —CHPh wherein in each instance Ph is unsubstituted or substituted with OH, COOH, alkyl wherein alkyl are from 1 to 4 carbon atoms, NH$_2$, NH(alkyl C$_{1-4}$) or NH(alkyl C$_{1-4}$)$_2$, or halogen such chlorine, fluorine, bromine or iodine or Q can be —CH$_2$ piperazino or —CH piperazino; and wherein when R$^5$ is Ph, R$^1$, R$^2$, R$^3$, and R$^4$ are not methyl or ethyl and wherein when R$^5$ is Ph, E is O, and Q is H, then R$^3$ and R$^4$ are not phenyl.

11. A compound as set forth in claim 10 wherein said metal is a paramagnetic metal selected from the group including Fe and Mn, said compound being stable in aqueous solutions, serum or other body fluids.

12. A compound as set forth in claim 10 including a 1:1 metal to ligand ratio.

13. A compound for use as a diagnostic or therapeutic pharmaceutical, or MRI contrast agent, said compound comprising: a phosphine core, and at least three hydrazine groups forming a tris-hydrazine phosphine ligand bound to a transition metal extending from said phosphorous core of the formula

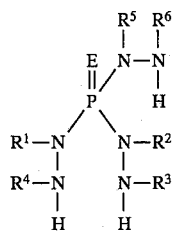

wherein $R^1, R^2, R^3, R^4$ are all the same or different and are H, an alkyl selected from Me, Et, n- or i-propyl, n-, i- or t-butyl, n-hexyl, a cyclohexyl, an alkylamine selected from —$NMe_2$, NHMe, $(CH_2)_nNMe_2$, $(CH_2)_nNHMe$, —$(CH_2)_nNH_2$, an alkoxy selected from —$O(CH_2)_nCH_3$, $(CH_2)_nOCH_3$, an aromatic of formula —$C_6H_4R$ wherein R=H, $NH_2$, COOH, NCS, CHO, activated esters, acid anhydrides, N-hydroxy succinamide, and $SiMe_3$; $R^5, R^6$ are all the same or different and are H, Me or Ph; and E is O or S.

* * * * *